United States Patent
Xu et al.

(10) Patent No.: US 10,604,466 B1
(45) Date of Patent: Mar. 31, 2020

(54) METHOD FOR PREPARING RESVERATROL COMPOUND

(71) Applicants: HANGZHOU NORMAL UNIVERSITY, Hangzhou (CN); Great Forest Biomedical Ltd., Hangzhou (CN)

(72) Inventors: Weiming Xu, Hangzhou (CN); Wanmei Li, Hangzhou (CN); Xiaoling Li, Hangzhou (CN); Pengfei Zhang, Hangzhou (CN); Jinsong Wang, Hangzhou (CN); Kejie Chai, Hangzhou (CN)

(73) Assignees: HANGZHOU NORMAL UNIVERSITY, Hangzhou (CN); GREAT FOREST BIOMEDICAL LTD., Hangzhou (CN)

( * ) Notice: Subject to any disclaimer, the term of this patent is extended or adjusted under 35 U.S.C. 154(b) by 0 days.

(21) Appl. No.: 16/561,242

(22) Filed: Sep. 5, 2019

(30) Foreign Application Priority Data

Apr. 28, 2019 (CN) .......................... 2019 1 0349597

(51) Int. Cl.
| | |
|---|---|
| *C07C 37/20* | (2006.01) |
| *C07C 37/84* | (2006.01) |
| *C07C 37/60* | (2006.01) |
| *C07C 37/00* | (2006.01) |
| *B01J 25/02* | (2006.01) |
| *B01J 23/44* | (2006.01) |
| *C07C 45/45* | (2006.01) |

(52) U.S. Cl.
CPC ............... *C07C 37/84* (2013.01); *B01J 23/44* (2013.01); *B01J 25/02* (2013.01); *C07C 37/002* (2013.01); *C07C 37/20* (2013.01); *C07C 37/60* (2013.01); *C07C 45/45* (2013.01)

(58) Field of Classification Search
None
See application file for complete search history.

(56) References Cited

PUBLICATIONS

Qian, Y-P. et al. "Antioxidant-Based Lead Discovery for Cancer Chemoprevention: The Case of Resveratrol" J. Med. Chem. 2009, 52, 1963-1974 with supporting information pp. S1-S21 (Year: 2009).*
Fernandes, T. A. et al. "Dioxomolybdenum Complexes as Excellent Catalysts for the Deoxygenation of Aryl Ketones to Aryl Alkenes" ChemCatChem 2015, 7, 3503-3507 (Year: 2015).*

* cited by examiner

*Primary Examiner* — Medhanit W Bahta
(74) *Attorney, Agent, or Firm* — Pearne & Gordon LLP

(57) ABSTRACT

The present invention provides a method for preparing a resveratrol compound, and belongs to the technical field of organic synthesis. In the present invention, first alkoxy-substituted benzyl halide, alkoxy-substituted benzaldehyde and a metal catalyst are subjected to oxidative addition and reduction elimination reactions to obtain alkoxy-substituted diphenylethanone; and then the alkoxy-substituted diphenylethanone and a metal catalyst are subjected to reduction, trans elimination and selective debenzylation reactions under a hydrogen atmosphere to obtain the resveratrol compound. In the preparation method of the present invention, the hydrogenation reduction, trans elimination and selective debenzylation reactions can be achieved just by a one-pot process, where the reaction directly obtains a trans olefin, thereby avoiding the formation of a isomer; and also the reaction selectively catalyzes debenzylation to eliminate Lewis acids from the source, and has the advantage of a high yield. Therefore, this process is a green and environmentally friendly process. The experimental results show that, the products obtained by the preparation method as provided by the present invention are all trans olefins, with the purity being up to more than 99.5%, and each yield being greater than 80%.

13 Claims, 5 Drawing Sheets

METHOD FOR PREPARING RESVERATROL COMPOUND

This application claims priority to Chinese application number 201910349597.3, filed Apr. 28, 2019, with a title of METHOD FOR PREPARING RESVERATROL COMPOUND. The above-mentioned patent application is incorporated herein by reference in its entirety.

TECHNICAL FIELD

The present invention relates to the technical field of organic synthesis, and in particular to a method for preparing a resveratrol compound.

BACKGROUND

Resveratrol products are a class of non-flavonoid polyphenolic compounds containing a stilbene structure, and include resveratrol, pterostilbene, oxidized resveratrol, piceatannol, and the like. They are antioxidants that are naturally found in grapes, mulberries, peanuts and *Polygonum cuspidatum*. Resveratrol, since the introduction of it, has been widely used in fields such as medicine, health care products and the like due to its good anti-inflammatory, anti-cancer and anti-oxidation effects. The newest study has shown that, pterostilbene exhibits a moderate inhibitory effect on cyclooxygenase COX-1, but has only weak inhibitory activity on COX-2, and the anti-inflammatory and antibacterial effects of pterostilbene are more obvious, where the antifungal activity of pterostilbene is more than 5 times greater than that of resveratrol. Resveratrol derivatives have better qualities and stronger physiological activities than those of resveratrol, so that the research of such products has attracted wide attention from the scientific community and publicity all around the world.

The existing literatures have reported on a method for synthesizing a resveratrol compound, mainly including subjecting alkoxy aryl aldehyde and ylide or phosphonate to a Wittig-Homer reaction to obtain a resveratrol ether compound, and finally subjecting the resveratrol ether compound to a dealkylation reaction to synthesize the resveratrol compound. However, this method has disadvantages of a carbon-carbon double bond configuration that is difficult to determine, poor selectivity of the resveratrol ether, poor deprotection selectivity and the like, which restricts the development of this method. Moreover, the prior art generally uses boron halides and aluminum halides as dealkylation agents, which have relatively larger environmental pollution. Moreover, such substances are highly irritant, and decompose or even cause explosion when exposed to water, and thus there are certain safety hazards.

SUMMARY

An objective of the present invention is to provide a method for preparing a resveratrol compound, which has the advantages of good selectivity, high yield and high safety, and is a green and environment friendly process.

To achieve the above purpose, the present invention provides the following technical solution.

A method for preparing a resveratrol compound includes the following steps:

(1) subjecting alkoxy-substituted benzyl halide, alkoxy-substituted benzaldehyde and a metal catalyst to oxidative addition and reduction elimination reactions to obtain alkoxy-substituted diphenylethanone; and (2) subjecting the alkoxy-substituted diphenylethanone and a metal catalyst to reduction, trans elimination and selective debenzylation reactions under a hydrogen atmosphere to obtain the resveratrol compound.

Preferably, the mole ratio of the alkoxy-substituted benzyl halide to the alkoxy-substituted benzaldehyde is 0.95-1.05:1.

Preferably, the metal catalysts of steps (1) and (2) are each independently at least one of palladium-carbon and Raney-nickel.

Preferably, the mass ratio of the metal catalysts of steps (1) and (2) to the alkoxy-substituted benzaldehyde is independently 0.01-0.1:1.

Preferably, for the oxidative addition and reductive elimination reactions, the temperature is 60-120° C. and the time is 3-9 h.

Preferably, the solvents for the oxidative addition and reductive elimination reactions and for the reduction, trans-elimination and selective debenzylation reactions are independently one or more of ethanol, isopropanol, isobutanol, sec-butanol, ethyl acetate, cyclohexane and toluene.

Preferably, for the reduction, trans-elimination and selective debenzylation reactions, the temperature is 80-150° C. and the time is 3-12 h.

Preferably, the hydrogen pressure for the reduction, trans-elimination and selective debenzylation reactions is 2-15 kg·f/cm$^2$.

Preferably, the preparation method further includes the following steps:

filtering the reaction solution obtained from the reduction, trans-elimination and selective debenzylation reactions, and then evaporating the filtrate to dryness to recrystallize the resultant solid, so as to obtain the resveratrol compound.

Preferably, the solvent used for the recrystallization is toluene.

The present invention provides a method for preparing a resveratrol compound, including the following steps: (1) subjecting alkoxy-substituted benzyl halide, alkoxy-substituted benzaldehyde and a metal catalyst to oxidative addition and reduction elimination reactions to obtain alkoxy-substituted diphenylethanone; and (2) subjecting the alkoxy-substituted diphenylethanone and a metal catalyst to reduction, trans elimination and selective debenzylation reactions under a hydrogen atmosphere to obtain the resveratrol compound. In the preparation method of the present invention, the hydrogenation reduction, trans elimination and selective debenzylation reactions can be achieved just by a one-pot process, where the reaction directly obtains a trans olefin, thereby avoiding the formation of a isomer; and also the reaction selectively catalyzes debenzylation to eliminate Lewis acids from the source, and has the advantage of a high yield. Therefore, this process is a green and environmentally friendly process. The experimental results show that, the products obtained by the preparation method as provided by the present invention are all trans olefins, with the purity being up to more than 99.5%, and each yield being greater than 80%.

DETAILED DESCRIPTION

Figure 1:
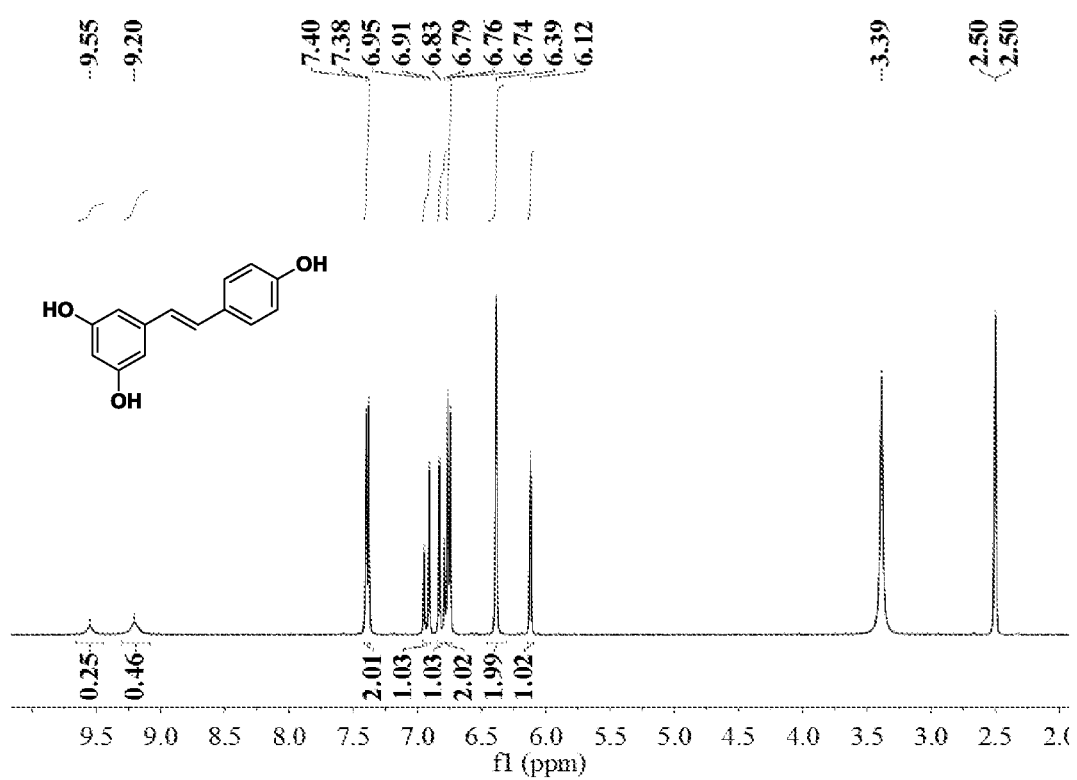
FIG. 1 is a hydrogen spectrogram of the product obtained in Embodiment 1.

The present invention provides a method for preparing a resveratrol compound, including the following steps:

(1) subjecting alkoxy-substituted benzyl halide, alkoxy-substituted benzaldehyde and a metal catalyst to oxidative addition and reduction elimination reactions to obtain alkoxy-substituted diphenylethanone; and (2) subjecting the alkoxy-substituted diphenylethanone and a metal catalyst to reduction, trans elimination and selective debenzylation reactions under a hydrogen atmosphere to obtain the resveratrol compound.

The reaction formula of the preparation method provided by the present invention is as shown in formula (1):

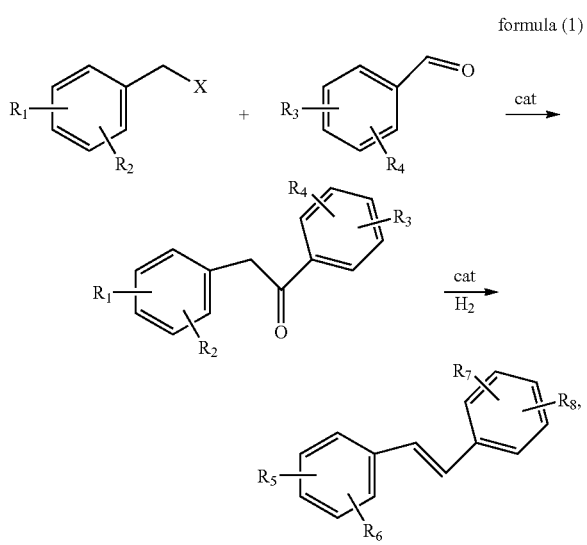

formula (1)

where, X is Cl, Br or I, $R_1$ and $R_3$ are each independently methoxy or benzyloxy, $R_2$ and $R_4$ are each independently methoxy, benzyloxy, or hydrogen, $R_5$ and $R_7$ are each independently methoxy or hydroxy, and $R_6$ and $R_8$ are each independently methoxy, hydroxy or hydrogen. In the preparation method of the present invention, the hydrogenation reduction, trans elimination and selective debenzylation reactions can be achieved just by a one-pot process, where the reaction directly obtains a trans olefin, thereby avoiding the formation of a isomer; and also the reaction selectively catalyzes debenzylation to eliminate Lewis acids from the source, and has the advantage of a high yield. Therefore, this process is a green and environmentally friendly process.

First, the alkoxy-substituted benzyl halide, the alkoxy-substituted benzaldehyde and the metal catalyst are subjected to oxidative addition and reduction elimination reactions to obtain the alkoxy-substituted diphenylethanone. In the present invention, said alkoxy-substituted benzyl halide is a benzyl halide containing at least one substituent group selected from a methoxy group and a benzyloxy group, said alkoxy-substituted benzaldehyde is a benzaldehyde containing at least one substituent group selected from a methoxy group and a benzyloxy group; the structure of said alkoxy-substituted benzyl halide is preferably as shown in formula I, and the structure of said alkoxy-substituted benzaldehyde is preferably as shown in formula II,

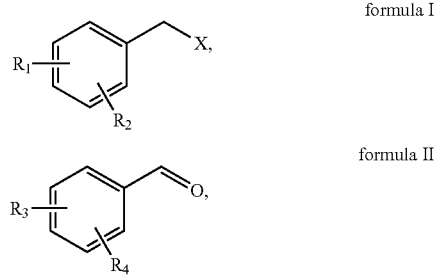

formula I formula II where X is Cl, Br or I, $R_1$ and $R_3$ are each independently methoxy or benzyloxy, and the $R_2$ and $R_4$ are each independently methoxy, benzyloxy, or hydrogen.

In the present invention, the alkoxy-substituted benzyl halide is preferably 3,5-dibenzyloxybenzyl chloride, 3,5-dimethoxybenzyl chloride, 3,5-dimethoxybenzyl bromide, 3, 5-dimethoxybenzyl iodide or 4-benzyloxybenzyl chloride; and the alkoxy-substituted benzaldehyde is preferably 4-benzyloxybenzaldehyde, 2,4-dibenzyloxy benzaldehyde, 3,4-dibenzyloxybenzaldehyde, or 3,5-dimethoxybenzaldehyde.

In the present invention, the mole ratio of the alkoxy-substituted benzyl halide to the alkoxy-substituted benzaldehyde is preferably 0.95-1.05:1.

In the present invention, the metal catalyst is preferably at least one of palladium-carbon and Raney-nickel; the present invention has no specific limitation on the palladium content in the palladium-carbon and the nickel content in the Raney-nickel, and a conventional content can be used; in the embodiments of the present invention, the palladium content in the palladium-carbon is preferably 5-20 wt %, and the nickel content in the Raney-nickel is preferably 40-60 wt %.

In the present invention, in the oxidative addition and reduction elimination reactions, the mass ratio of the metal catalyst to the alkoxy-substituted benzaldehyde is preferably 0.01-0.1:1.

In the present invention, the solvent for the oxidative addition and reduction elimination reactions is preferably one or more of ethanol, isopropanol, isobutanol, sec-butanol, ethyl acetate, cyclohexane and toluene, and when the solvent includes multiple solvents, there is no specific limitation on the ratio of the multiple solvents, and any ratio may be used; and the mass ratio of the solvent to the alkoxy-substituted benzaldehyde is preferably 5-15:1.

In the present invention, for the oxidative addition and reduction elimination reactions, the temperature is preferably 60-120° C., and more preferably 80-90° C.; and the time is preferably 3-9 h, and more preferably 4-5 h.

After the alkoxy-substituted diphenylethanone is obtained, the alkoxy-substituted diphenylethanone and a metal catalyst are subjected to reduction, trans elimination and selective debenzylation reactions under a hydrogen atmosphere to obtain the resveratrol compound. The specific mechanism of this reaction step is as shown in formula (2):

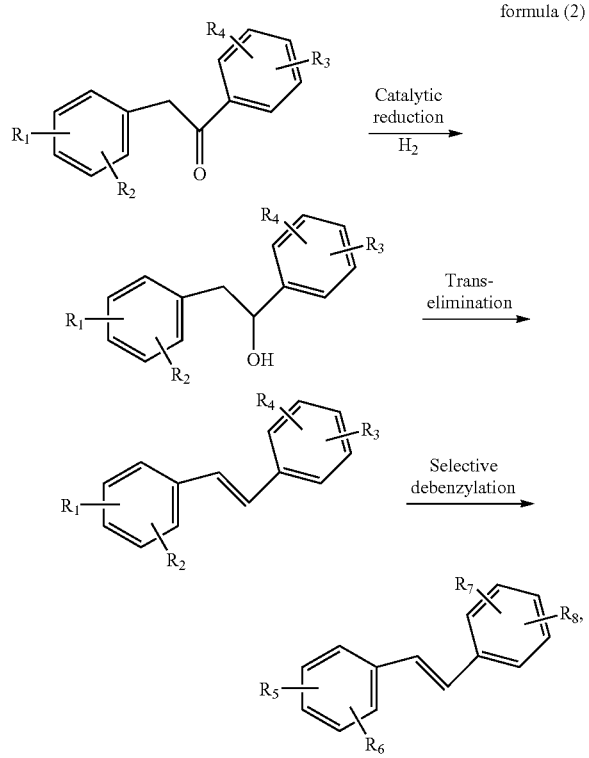

formula (2)

where $R_1$ and $R_3$ are each independently methoxy or benzyloxy, $R_2$ and $R_4$ are each independently methoxy, benzyloxy, or hydrogen, $R_5$ and $R_7$ are each independently methoxy or hydroxy, and $R_6$ and $R_8$ are each independently methoxy, hydroxy or hydrogen. In the reaction of the formula (2), a carbonyl group in the alkoxy-substituted diphenylethanone is first catalytically reduced to a hydroxyl group, and the Newman projection formula of the obtained product is more favorable for the generation of a trans-olefin, and thus the reaction can only obtain the trans-olefin, a benzyloxy group is then selectively removed from the trans-olefin to convert the benzyloxy group into a hydroxy group while the methoxy group is retained; when no benzyloxy group is present, a trans product is directly obtained; and the selective debenzylation reaction means that a benzyloxy group is removed when the benzyloxy group is present, and the final product is directly obtained when no benzyloxy group is present.

In the present invention, the solvent for the reduction, trans-elimination and selective debenzylation reactions is preferably one or more of ethanol, isopropanol, isobutanol, sec-butanol, ethyl acetate, cyclohexane, and toluene, and when the solvent is multiple solvents, there is no specific limitation on the ratio of the multiple solvents, and any ratio may be used; and the use amount of the solvent is preferably the same as that of the solvent for the oxidation addition and reduction elimination reactions, and thus will not be repeated here anymore.

In the present invention, the type and use amount of the metal catalyst for the reduction, trans elimination and selective debenzylation reactions is preferably the same as those of the catalyst used for the oxidative addition and reduction elimination reactions, and thus will not be repeated here anymore.

In the implementation of the present invention, preferably the reaction solution obtained from the oxidative addition and reduction elimination reactions is directly subjected to the subsequent steps. Specifically, it is preferred that the reaction solution obtained from the oxidative addition and reduction elimination reactions is cooled to room temperature, and then is introduced with a hydrogen gas until a certain pressure is achieved, then heated to the temperature desired for the reduction, trans elimination and selective debenzylation reactions, to conduct the reduction, trans elimination and selective debenzylation reactions.

In the present invention, for the reduction, trans elimination and selective debenzylation reactions, the temperature is preferably 80-150° C., and more preferably 100-120° C.; and the time is preferably 3-12 h, and more preferably 5-6 h; the hydrogen pressure for the reduction, trans elimination, and selective debenzylation reactions (the pressure when the reaction solution is at room temperature) is preferably 2-15 kg·f/cm$^2$, and more preferably 4-6 kg·f/cm$^2$.

In the present invention, the method preferably also includes the following step:

filtering the reaction solution obtained from the reduction, trans-elimination and selective debenzylation reactions, and then evaporating the filtrate to dryness to recrystallize the resultant solid, so as to obtain the resveratrol compound.

In the present invention, the solvent used for the recrystallization is preferably toluene; and the recrystallization preferably includes the following steps:

A hot solution of the solid in toluene was formulated, and then cooled to 5-15° C., and filtered.

In the present invention, the temperature of the hot toluene solution is preferably 80-90° C.

In the present invention, after the recrystallization is completed, it preferably includes drying.

The method for preparing the resveratrol compound as provided by the present invention is described in detail below in connection with Embodiments, but these Embodiments should not be understood as limiting the claimed scope of the present invention.

Embodiment 1

67.7 g of 3,5-dibenzyloxy benzyl chloride, 42.4 g of 4-benzyloxy benzaldehyde, 2 g of a 5 wt % palladium-carbon catalyst and 400 g of isopropanol were mixed and heated to 80° C. for reacting for 4 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 100° C. and continually reacted for 5 hours; and the obtained reaction solution was filtered to recover a catalyst, the filtrate was evaporated to dryness, the solid obtained from the evaporation to dryness was dissolved with 50 g of toluene while heated to 80° C., then cooled to 10° C., filtered and dried to obtain 40.5 g of resveratrol, with the yield being 88.8%, and the purity being 99.6% as tested by liquid chromatography.

Figure 2:
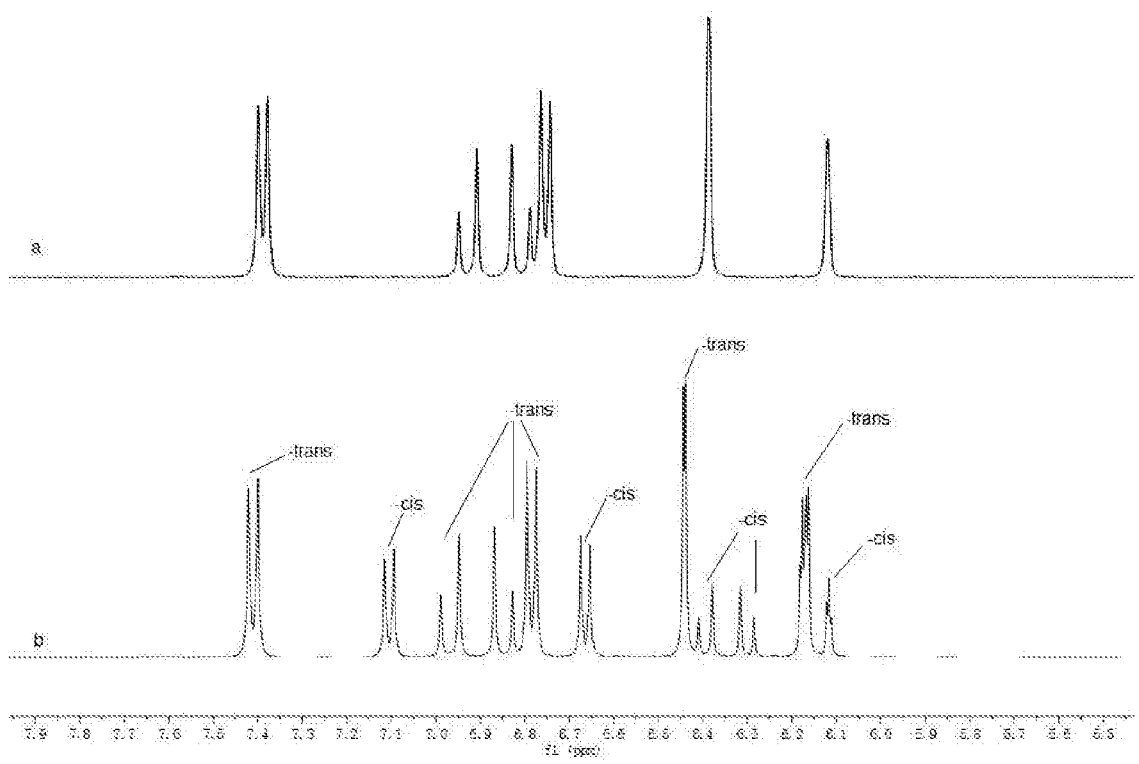
FIG. 2 is a hydrogen spectrogram of a trans-resveratrol and a hydrogen spectrogram of mixed cis and trans resveratrols.

The product obtained in this Embodiment was subjected to nuclear magnetic characterization, and its hydrogen spectrogram was as shown in FIG. 1, which was compared with FIG. 2 (where a was the hydrogen spectrogram of trans-resveratrol, and b was the hydrogen spectrogram of mixed cis and trans resveratrols). Therefore, it could be seen that the product obtained by the present invention contained only the trans structure, indicating that the product was only of a trans structure.

Embodiment 2

37.3 g of 3,5-dimethoxybenzyl chloride, 42.4 g of 4-benzyloxy benzaldehyde, 4.24 g of a 5 wt % palladium-carbon catalyst and 400 g of toluene were mixed and heated to 120° C. for reacting for 3 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 150° C. and continually reacted for 3 hours; and the obtained reaction solution was filtered to recover a catalyst, the filtrate was evaporated to dryness, the solid obtained from the evaporation to dryness was dissolved with 50 g of toluene while heated to 85° C., then cooled to 5° C., filtered and dried to obtain 44.5 g of pterostilbene, with the yield being 86.9%, and the purity being 99.5% as tested by liquid chromatography.

Figure 3:
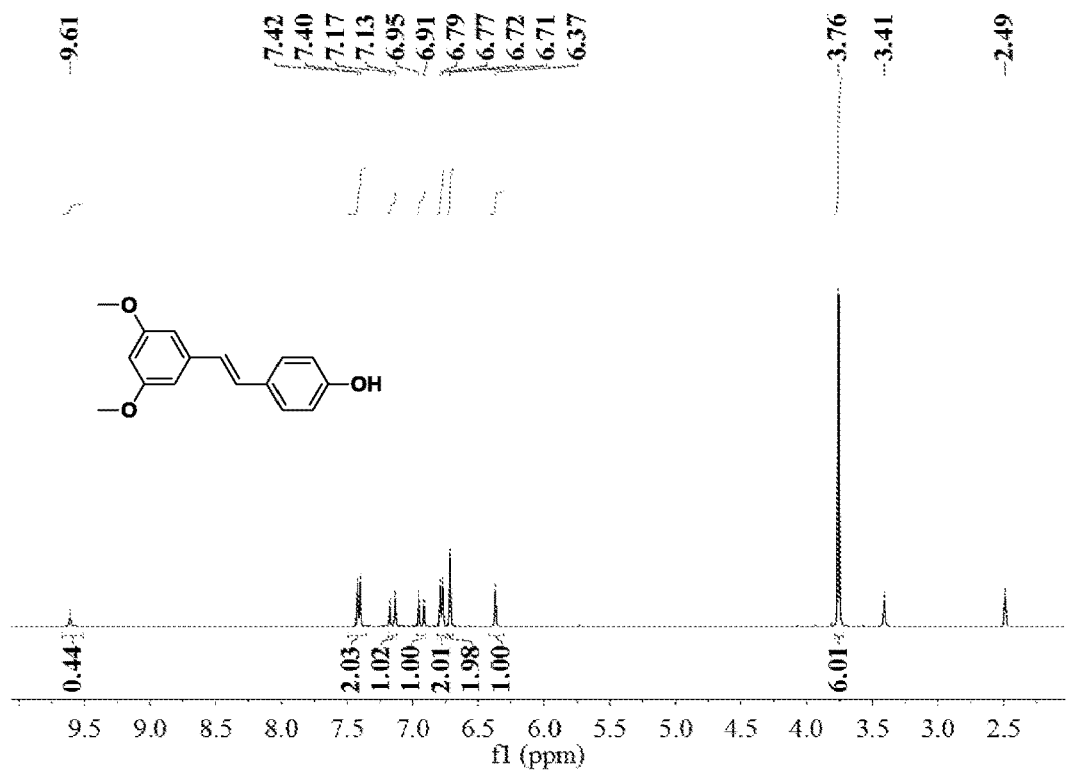
FIG. 3 is a hydrogen spectrogram of the product obtained in Embodiment 2.

The product obtained in this embodiment was subjected to nuclear magnetic characterization, and its hydrogen spectrogram was as shown in FIG. 3. It can be seen from FIG. 3 that, the resultant pterostilbenes are each of a trans structure.

Embodiment 3

67.7 g of 3,5-dibenzyloxy benzyl chloride, 63.6 g of 2,4-dibenzyloxy benzaldehyde, 0.64 g of a 20 wt % palladium-carbon catalyst and 400 g of toluene were mixed and heated to 60° C. for reacting for 9 hours, and then the obtained reaction solution was cooled to below 25° C.; the gas in the reaction vessel was replaced with a hydrogen gas, and then introduced with the hydrogen gas until the pressure was 15 kg·f/cm$^2$, and then heated to 80° C. and continually reacted for 12 hours; and the obtained reaction solution was filtered to recover a catalyst, the filtrate was evaporated to dryness, the solid obtained from the evaporation to dryness was dissolved with 50 g of toluene while heated to 80° C., then cooled to 15° C., filtered and dried to obtain 40.1 g of oxidized resveratrol, with the yield being 82.2%, and the purity being 99.8% as tested by liquid chromatography.

Figure 4:
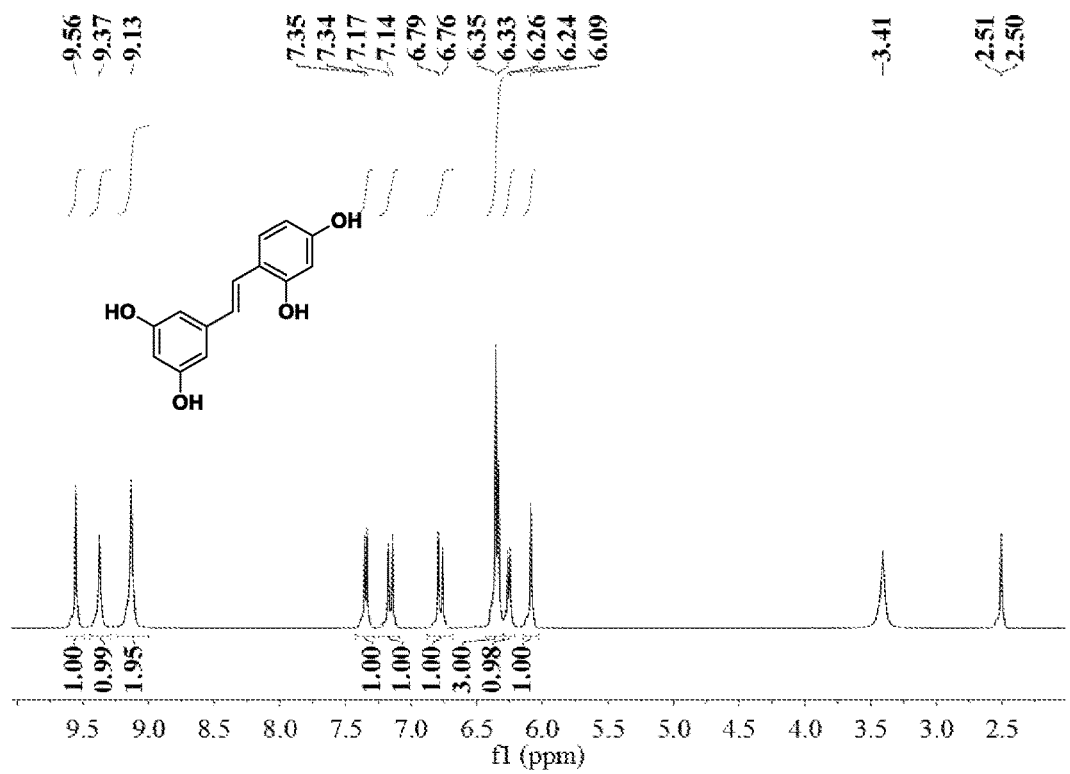
FIG. 4 is a hydrogen spectrogram of the product obtained in Embodiment 3.

The product obtained in this embodiment was subjected to nuclear magnetic characterization, and its hydrogen spectrogram was as shown in FIG. 4. It can be seen from FIG. 4 that, the resultant oxidized resveratrols are each of a trans structure.

Embodiment 4

67.7 g of 3,5-dibenzyloxy benzyl chloride, 63.6 g of 3,4-dibenzyloxy benzaldehyde, 6.36 g of a 10 wt % palladium-carbon catalyst and 400 g of ethyl acetate were mixed and heated to 80° C. for reacting for 9 hours, and then the obtained reaction solution was cooled to below 25° C.; the gas in the reaction vessel was replaced with a hydrogen gas, and then introduced with the hydrogen gas until the pressure was 2 kg·f/cm$^2$, and then heated to 100° C. and continually reacted for 12 hours; and the obtained reaction solution was filtered to recover a catalyst, the filtrate was evaporated to dryness, the solid obtained from the evaporation to dryness was dissolved with 50 g of toluene while heated to 80° C., then cooled to 10° C., filtered and dried to obtain 41.2 g of piceatannol, with the yield being 84.4%, and the purity being 99.5% as tested by liquid chromatography.

Figure 5:
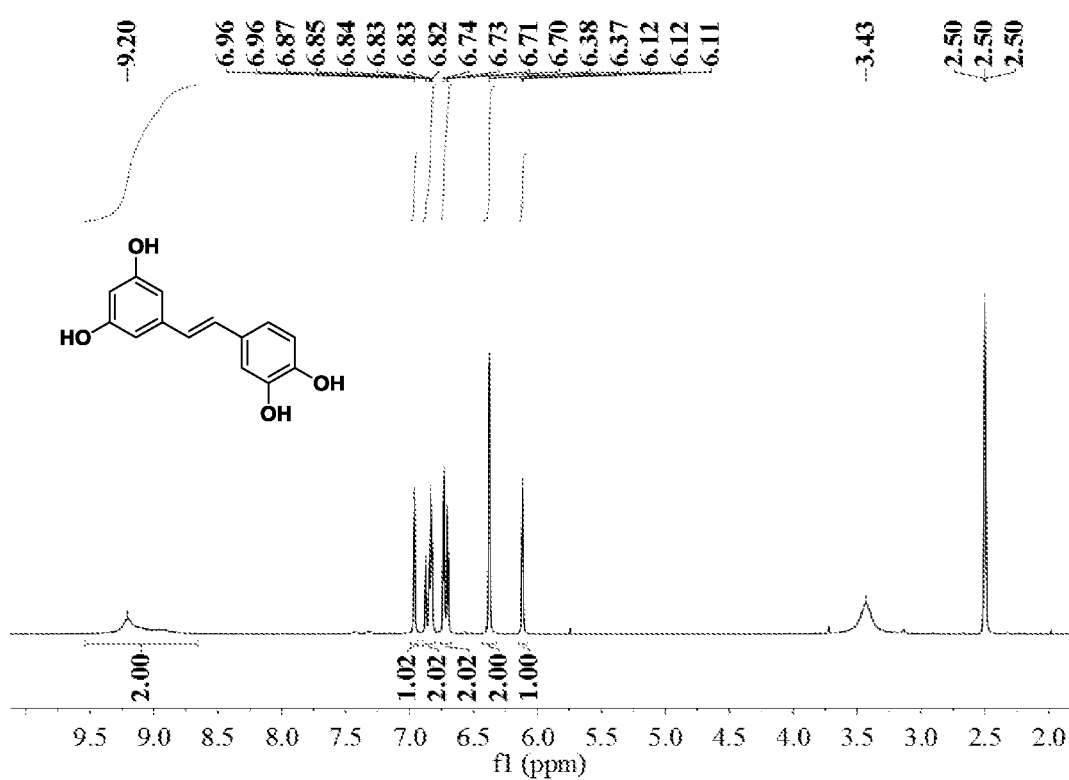
FIG. 5 is a hydrogen spectrogram of the product obtained in Embodiment 4.

The product obtained in this embodiment was subjected to nuclear magnetic characterization, and its hydrogen spectrogram was as shown in FIG. 5. It can be seen from FIG. 5 that, the resultant piceatannols are each of a trans structure.

Embodiment 5

37.3 g of 3,5-dimethoxybenzyl chloride, 27.2 g of 4-methoxybenzaldehyde, 2 g of a 5 wt % palladium-carbon catalyst and 408 g of toluene were mixed and heated to 80° C. for reacting for 5 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 120° C. and continually reacted for 6 hours; and the obtained reaction solution was filtered to recover a catalyst, the filtrate was evaporated to dryness, the solid obtained from the evaporation to dryness was dissolved with 50 g of toluene while heated to 90° C., then cooled to 10° C., filtered and dried to obtain 50.4 g of resveratrol trimethyl ether, with the yield being 93.3%, and the purity being 99.5% as tested by liquid chromatography.

Figure 6:
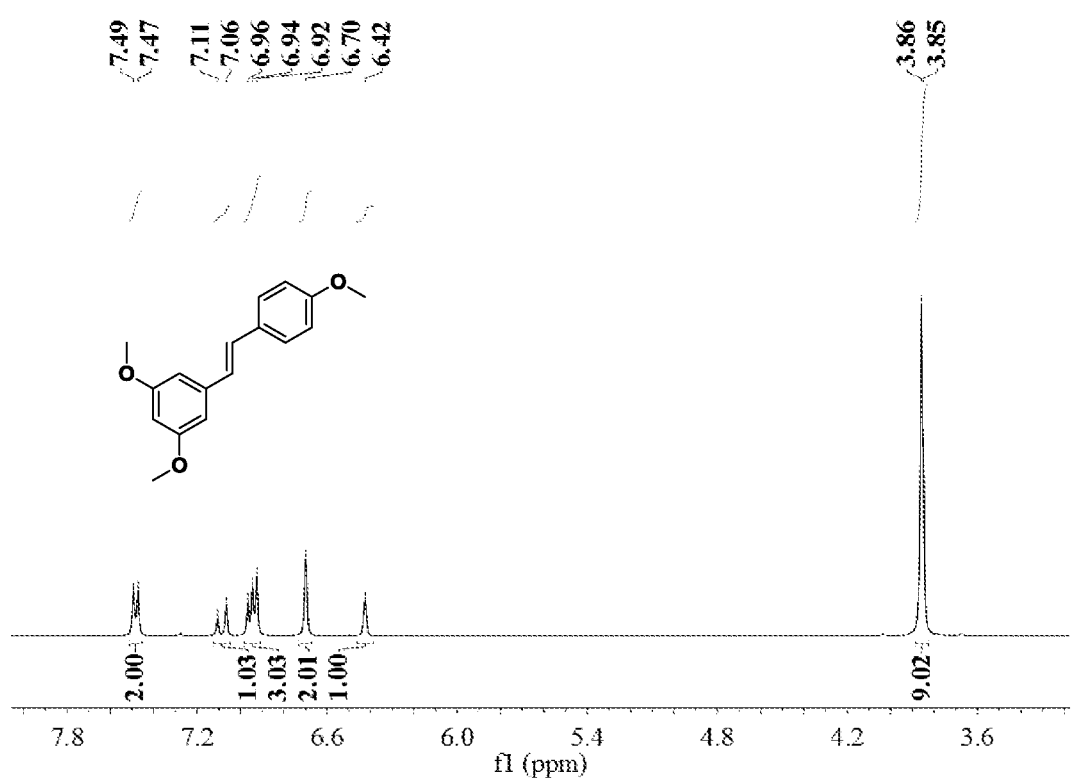
FIG. 6 is a hydrogen spectrogram of the product obtained in Embodiment 5.

The product obtained in this embodiment was subjected to nuclear magnetic characterization, and its hydrogen spectrogram was as shown in FIG. 6. It can be seen from FIG. 6 that, the resultant resveratrol trimethyl ethers are each of a trans structure.

Embodiment 6

35.4 g of 3,5-dimethoxybenzyl chloride, 27.2 g of 4-methoxybenzaldehyde, 2 g of a 5 wt % palladium-carbon catalyst, 250 g of isobutanol and 200 g of sec-butanol were mixed and heated to 80° C. for reacting for 5 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 120° C. and continually reacted for 6 hours; and the obtained reaction solution was filtered to recover a catalyst, the filtrate was evaporated to dryness, the solid obtained from the evaporation to dryness was dissolved with 50 g of toluene while heated to 90° C., then cooled to 10° C., filtered and dried to obtain 49.0 g of resveratrol trimethyl ether, with the yield being 90.7%, and the purity being 99.6% as tested by liquid chromatography.

The product obtained in this embodiment was subjected to nuclear magnetic characterization, and its hydrogen spectrogram was the same as that shown in FIG. 6, indicating that the resultant resveratrol trimethyl ethers are each of a trans structure.

Embodiment 7

39.2 g of 3,5-dimethoxybenzyl chloride, 27.2 g of 4-methoxybenzaldehyde, 1 g of a Raney-nickel catalyst that has a nickel content of 40 wt %, 250 g of cyclohexane and 200 g of ethanol were mixed and heated to 80° C. for reacting for 40 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 90° C. and continually reacted for 6 hours; and the obtained reaction solution was filtered to recover a catalyst, the filtrate was evaporated to dryness, the solid obtained from the evaporation to dryness was dissolved with 50 g of toluene while heated to 90° C., then cooled to 10° C., filtered and dried to obtain 49.8 g of resveratrol trimethyl ether, with the yield being 92.2%, and the purity being 99.5% as tested by liquid chromatography.

The product obtained in this embodiment was subjected to nuclear magnetic characterization, and its hydrogen spectrogram was the same as that shown in FIG. 6, indicating that the resultant resveratrol trimethyl ethers are each of a trans structure.

Embodiment 8

46.2 g of 3,5-dimethoxybenzyl bromide, 42.4 g of 4-benzyloxy benzaldehyde, 3 g of a 5 wt % palladium-carbon catalyst and 400 g of toluene were mixed and heated to 100° C. for reacting for 5 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 120° C. and continually reacted for 4 hours; and the obtained reaction solution was filtered to recover a catalyst, the filtrate was evaporated to dryness, the solid obtained from the evaporation to dryness was dissolved with 50 g of toluene while heated to 85° C., then cooled to 10° C., filtered and dried to obtain 44.1 g of pterostilbene, with the yield being 86.1%, and the purity being 99.5% as tested by liquid chromatography.

The product obtained in this embodiment was subjected to nuclear magnetic characterization, and its hydrogen spectrogram was the same as that shown in FIG. 3, indicating that the resultant pterostilbenes are each of a trans structure.

Embodiment 9

55.6 g of 3,5-dimethoxybenzyl iodide, 42.4 g of 4-benzyloxy benzaldehyde, 3 g of a 5 wt % palladium-carbon catalyst and 400 g of toluene were mixed and heated to 100° C. for reacting for 5 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 120° C. and continually reacted for 4 hours; and the obtained reaction solution was filtered to recover a catalyst, the stock solution was evaporated to dryness, the solid obtained from the evaporation to dryness was dissolved with 50 g of toluene while heated to 85° C., then cooled to 10° C., filtered and dried to obtain 44.6 g of pterostilbene, with the yield being 87.1%, and the purity being 99.5% as tested by liquid chromatography.

The product obtained in this embodiment was subjected to nuclear magnetic characterization, and its hydrogen spectrogram was the same as that shown in FIG. 3, indicating that the resultant pterostilbenes are each of a trans structure.

Embodiment 10

Preparation of Pterostilbene 46.5 g of 4-benzyloxy benzyl chloride, 33.2 g of 3,5-dimethoxybenzaldehyde, 2 g of a 5 wt % palladium-carbon catalyst and 400 g of toluene were mixed and heated to 100° C. for reacting for 5 hours, and then the obtained reaction solution was cooled to below 25° C.; the gas in the reaction vessel was replaced with a hydrogen gas, and then introduced with the hydrogen gas until the pressure was 8 kg·f/cm$^2$, and then heated to 120° C. and continually reacted for 4 hours; and the obtained reaction solution was filtered to recover a catalyst, the stock solution was evaporated to dryness, the solid obtained from the evaporation to dryness was dissolved with 50 g of toluene while heated to 85° C., then cooled to 10° C., filtered and dried to obtain 45.5 g of pterostilbene, with the yield being 88.9%, and the purity being 99.6% as tested by liquid chromatography.

The product obtained in this embodiment was subjected to nuclear magnetic characterization, and its hydrogen spectrogram was the same as that shown in FIG. 3, indicating that the resultant pterostilbenes are each of a trans structure.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for preparing a resveratrol compound, comprising the following steps:
    (1) subjecting alkoxy-substituted benzyl halide, alkoxy-substituted benzaldehyde and a metal catalyst to oxidative addition and reduction elimination reactions to obtain alkoxy-substituted diphenylethanone; and
    (2) subjecting the alkoxy-substituted diphenylethanone and a metal catalyst to reduction, trans elimination and selective debenzylation reactions under a hydrogen atmosphere to obtain the resveratrol compound.

2. The preparation method according to claim 1, wherein the mole ratio of the alkoxy-substituted benzyl halide to the alkoxy-substituted benzaldehyde is 0.95-1.05:1.

3. The preparation method according to claim 1, wherein the metal catalysts of steps (1) and (2) are each independently at least one of palladium-carbon and Raney-nickel.

4. The preparation method according to claim 1, wherein the mass ratio of the metal catalyst of step (1) to the alkoxy-substituted benzaldehyde is 0.01-0.1:1.

5. The preparation method according to claim 1, wherein for the oxidative addition and reductive elimination reactions, the temperature is 60-120° C. and the time is 3-9 h.

6. The preparation method according to claim 1, wherein the solvents for the oxidative addition and reductive elimination reactions and for the reduction, trans-elimination and selective debenzylation reactions are independently one or more of ethanol, isopropanol, isobutanol, sec-butanol, ethyl acetate, cyclohexane and toluene.

7. The preparation method according to claim 1, wherein for the reduction, trans-elimination and selective debenzylation reactions, the temperature is 80-150° C. and the time is 3-12 h.

8. The preparation method according to claim 1, wherein the hydrogen pressure for the reduction, trans-elimination and selective debenzylation reactions is 2-15 kg·f/cm$^2$.

9. The preparation method according to claim 1, further comprising the following steps:
    filtering the reaction solution obtained from the reduction, trans-elimination and selective debenzylation reactions, and then evaporating the filtrate to dryness to recrystallize the resultant solid, so as to obtain the resveratrol compound.

10. The preparation method according to claim 9, wherein the solvent used for the recrystallization is toluene.

11. The preparation method according to claim 3, wherein the mass ratio of the metal catalyst of step (1) to the alkoxy-substituted benzaldehyde is 0.01-0.1:1.

12. The preparation method according to claim 5, wherein the solvents for the oxidative addition and reductive elimination reactions and for the reduction, trans-elimination and selective debenzylation reactions are independently one or more of ethanol, isopropanol, isobutanol, sec-butanol, ethyl acetate, cyclohexane and toluene.

13. The preparation method according to claim 7, wherein the hydrogen pressure for the reduction, trans-elimination and selective debenzylation reactions is 2-15 kg·f/cm$^2$.

* * * * *